(12) United States Patent
Martin et al.

(10) Patent No.: US 8,247,220 B2
(45) Date of Patent: Aug. 21, 2012

(54) OPTICAL INDICATOR FOR DETECTING BACTERIAL PATHOGENS

(75) Inventors: Stephanie M. Martin, Woodstock, GA (US); John G. MacDonald, Decatur, GA (US); Erica M. Phillips, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 778 days.

(21) Appl. No.: 12/332,843

(22) Filed: Dec. 11, 2008

(65) Prior Publication Data

US 2009/0197296 A1 Aug. 6, 2009

Related U.S. Application Data

(60) Provisional application No. 61/063,466, filed on Feb. 1, 2008.

(51) Int. Cl.
*C12M 3/00* (2006.01)
(52) U.S. Cl. ............... 435/287.7; 435/286.5; 435/287.1; 435/288.7; 435/7.32; 436/519
(58) Field of Classification Search ................. None
See application file for complete search history.

(56) References Cited

U.S. PATENT DOCUMENTS

| | | | |
|---|---|---|---|
| 4,336,337 A | 6/1982 | Wallis et al. | |
| 4,582,795 A | 4/1986 | Shibuya et al. | |
| 5,075,077 A | 12/1991 | Durley, III et al. | |
| 5,635,367 A | 6/1997 | Lund | |
| 6,528,325 B1 | 3/2003 | Hubscher et al. | |
| 6,824,997 B1 * | 11/2004 | Moore et al. | 435/7.34 |
| 7,399,608 B2 | 7/2008 | MacDonald et al. | |
| 2005/0130253 A1 * | 6/2005 | Lye et al. | 435/29 |
| 2006/0040408 A1 * | 2/2006 | Jones et al. | 436/518 |
| 2006/0223052 A1 | 10/2006 | MacDonald et al. | |
| 2007/0140971 A1 | 6/2007 | MacDonald et al. | |

OTHER PUBLICATIONS

Mersch, John, "Rapid Strep Test," MedicineNet.com, Internet web page "http://www.medicinenet.com/rapid_strep_test/article.htm", 2008, 1 page.
Rhodes, Monica, "Rapid Strep Test for Strep Throat," Yahoo!® Health, Internet web site "http://health.yahoo.com/infectiousdisease-diagnosis/rapid-strep-test-for-strep-throat/healthwise--hw54524.html", Aug. 8, 2008, 2 pages.

* cited by examiner

*Primary Examiner* — N. C. Yang
(74) *Attorney, Agent, or Firm* — Denise L. Stoker

(57) ABSTRACT

A clinical testing assay device that can differentiate bacterial from viral infections is described. The assay device has a sample contact zone with an absorbent pad on which a test sample is deposited and a detection zone with a colorant indicator that is sensitive to bacteria cells. The colorant indicator changes color when exposed to a bacteria sample. The color change signal can manifest relatively quickly, usually within a few minutes, and with an intensity correlative to the concentration of bacteria in a test sample. A method of use is also provided.

6 Claims, 10 Drawing Sheets

OPTICAL INDICATOR FOR DETECTING BACTERIAL PATHOGENS

RELATED APPLICATION

Applicants hereby claim priority from presently copending U.S. Provisional Application No. 61/063,466 entitled "Optical Indicator for Detecting Bacterial Pathogens" and filed on Feb. 1, 2008, in the names of Stephanie M. Martin, John G. MacDonald, and Erica M. Phillips.

FIELD OF INVENTION

The present invention relates to an optical indicator device that employs a solvatochromic colorant as part of a diagnostic tool to differentiate between bacterial and viral pathogens that cause infections. In particular, the invention involves a chemical reaction between bacteria and a colorant or dye-based indicator.

BACKGROUND

Often when first examining a patient, clinicians can find it difficult to differentiate between bacterial versus viral caused infections. About 30 million cases of tonsillopharyngitis are diagnosed every year, with viruses being the predominant cause of infection. Rhinovirus, adenovirus, coxsackievirus, echovirus, coronavirus, and Epstein-Barr viruses are the most common causes of viral tonsillopharyngitis. Misdiagnosis, however, often results in over-prescription of antibiotics, which is a growing public health concern due to the creation of antibiotic-resistant microbes. In fact, clinicians fail to distinguish between viral and bacterial infections of the throat approximately 50% of the time. Of the estimated 6.7 million pharyngeal-related adult visits to primary care providers each year, antibiotics are prescribed 70-75% of the time.

Throat cultures remain the "gold standard" for diagnosis, but results may not be available for up to 48 hours. Although relatively quick, use of rapid strep screening tests can be problematic due to an error rate of between 5-40%. In addition, the available rapid tests are only meant to diagnose group A beta hemolytic streptococci, even though other bacteria may be involved (such as *Neisseria gonorrhoeae, Corynebacterium diphtheriae, Haemophilus influenzae. Moraxella catarrhalis*, and group C and group G *streptococcus*). Group C *Streptococcus*, in particular, can be more common in college students and young adults and is not detected by the rapid strep tests. Typically, a negative test result is taken to mean the infection is most likely viral, but a culture is still taken and results may contradict the original rapid test result. The patient may have been prescribed antibiotics as a precaution while waiting for the culture results, or they may be called several days later and informed that they need to take antibiotics if the culture results come back positive. During that time, they may have unknowingly exposed others to the infection as well. Thus, a need exists for a test which would allow clinicians to rapidly and accurately distinguish between bacterial and viral throat infections.

Beyond the clinician's office, there is an even larger need for devices that provide additional information to the consumer. Absenteeism due to illness continues to burden businesses financially, accounting for 15% of payroll expenses, on average. When workers become ill, time is taken from their jobs not only to rest and recover, but often times to go to the doctor for a diagnosis and treatment. Moreover, workers may have to take time out of their schedule to bring their sick children to the doctor.

Because common viral infections which might cause a sore throat are not usually serious or helped by antibiotics, consumers might act differently if they had more information about their illness before going to the physician. Knowing in advance that their symptoms are more likely to be viral in nature might allow a consumer to save money and time on doctor visits and treat themselves properly with rest, fluids, and over-the-counter medicines. Similarly, being informed that an infection is most likely bacterial in nature could guide consumer behavior as well. An individual could be more informed about when they need to see a physician and also might have more reasonable expectations about the kinds of treatments which could help their condition (over-the-counter meds vs. prescription antibiotics, for example). Therefore, consumers could benefit greatly from devices which provide additional information about their symptoms and treatment options.

Hence, a need exists for an optical indicator that can differentiate between bacterial and viral pathogens. Further, an indicator device that can be easily used by in clinical or at-home settings. can help provide quick, accurate and consistent diagnostic or detection information for both healthcare providers and general consumers.

SUMMARY OF THE INVENTION

The present invention pertains to a simple detector or indicator device that uses a color change component to communicate information to a user. The device has a visually or optically sensitive colorant. Generally, the device has an absorbent pad, a colorant or dye-impregnated membrane (reaction pad) membrane, and a results viewing window housed in a singular package. The detection device can be a fast-acting clinical diagnostic aid, which a healthcare worker or consumer can use by swabbing a test sample from a patient, contacting the sample-containing swab to the absorbent pad, closing or securing (e.g., folding and sealing) the device according to directions, such that contact occurs between the dye-impregnated membrane (reaction pad) and the absorbent pad. One can then turn the device over to read a result through the sample results viewing window. A color reference may be provided next to the sample results viewing window as a comparison. A results data interpretation guide also may be provided on the back of the testing substrate. The colorant is sensitive to bacteria cells and insensitive to viruses, hence the diagnostic device can distinguish between bacterial and viral pathogens.

The present invention also pertains to a method of using an indicator device for assaying a bacterial infection. The method involves providing a testing device, such as described herein, applying a test sample to said sample contact zone; closing said first leaf against said second leaf, such that said absorbent pad contacts said colorant reaction zone; and observing for a color change to manifest in the results window. The device has a substrate with at least a first and a second opposing leaves, said first and second leaves each having an inner and outer surface, said first leaf having a sample contact zone with an absorbent pad situated on said first-leaf inner surface, said second leaf having a colorant reaction zone situated on said second-leaf inner surface opposite said sample contact zone, and a results windows on said second-leaf outer surface where a visual communication manifests. Optionally, a clinician or consumer may send or return the test devices to a test processing provider to obtain an interpretation of the results.

It is understood that both the foregoing summary and the following detailed description and examples are merely representative of the invention, and are intended to provide an overview for understanding the invention. Additional features and advantages of the present diagnostic indicator device and associated articles of manufacture and methods will be disclosed in the following detailed description.

BRIEF DESCRIPTION OF FIGURES

FIG. 1A shows a view of the outside surface of the panels (100a, 200a), while FIG. 1B shows a view of the inside of the panels (100b, 200b) on the opposite side as laid out flat.

FIG. 2A is a view of the exterior (100a, 200a, 300a) and FIG. 2B is a view of the opposite, interior of the three panels (100b, 200b, 300b) when unfolded in a flat plane.

FIG. 3A represents no change in color relative to the reference spot, hence a "Negative" result, while FIG. 3D represents a "Positive" result. The colorant discolors over a period of about 5-10 minutes, as illustrated by the transition in FIGS. 3B and 3C, from the original dye color to a pale yellow to white. FIG. 3D is a "strong" positive signal, while FIGS. 3F and 3E illustrate examples of various manifestations of "weak" positive results, as differentiated by the partial or relative intensity of the discoloration.

DETAILED DESCRIPTION OF THE INVENTION

A

Section I.—Device Structure

The present invention pertains to a clinical detection device that can provide a fast-reacting assay, which reliability can distinguish between bacterial and viral pathogens, which may cause various infections of the oral cavity, auditory canal, and upper respiratory passages. Generally, the detection device has an absorbent pad for receiving a test sample, a solvatochromic dye-containing membrane, and a results viewing area. When said absorbent pad having a test sample associated thereon contacts the solvatochromic dye, a visual signal manifests in the results viewing area. A change in color of the solvatochromic dye indicates the presence of a bacterial pathogen. Laboratory evidence supports a hypothesis that the color change results from a reaction between the bacterial cellular surface acidic residues with the solvatochromic dye. The visual signal can be read and quantified with an optical scanning device, such as presently available commercially. Furthermore, we believe that the bacterial cell wall is primarily responsible for this color change. Hence, the present invention provides a way of detecting whole cells of bacteria or large fragments of lysed bacteria cell walls. This attribute distinguishes the present invention from the current technology relating to lateral flow assays.

According to the invention, the diagnostic or test device has an absorbent pad in a sample contacting zone, an opposing detection zone having a solvatochromic dye, and a results visualizing window, such that a test sample applied to said absorbent pad contacts said opposing detection zone, reacts with a solvatochromic dye in the detection zone, and manifests a visual signal through a results visualizing window. The diagnostic device has a substrate that can be folded to have at least a first and a second opposing panels or leaves. The first and second leaves each have an inner and outer surface. A sample contact zone with an absorbent pad is situated on the inner surface of the first leaf. A colorant indicator zone is situated on the inner surface of the second leaf, which is opposite to the sample contact zone. A results window, where a visual communication manifests, is situated on the outer surface of the second leaf. In certain embodiments, the substrate is semi-rigid and bendable. The substrate further may include a third leaf that folds over in between the first and second leaves. The third leaf has a reaction aperture situated opposite the sample contact zone. When the three leaves are properly interfolded, the adsorbent pad in the sample contact zone, reaction aperture, colorant indicator zone, and results viewing window, respectively, all align with each other along an axis.

Figure 1A:
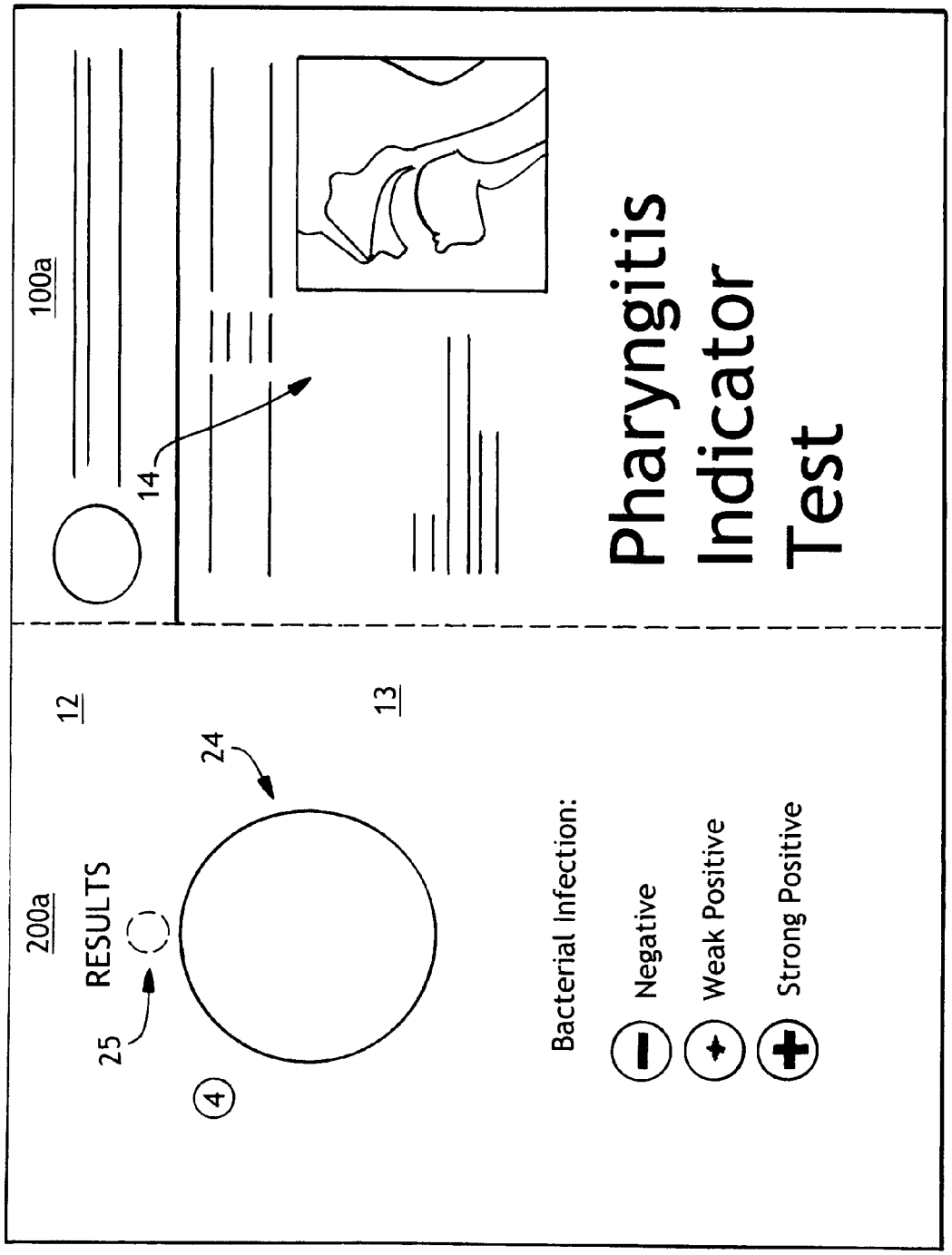
FIGS. 1A and 1B are planar illustrations of an embodiment of the present indicator device having first (100) and second panels (200).
Figure 1B:
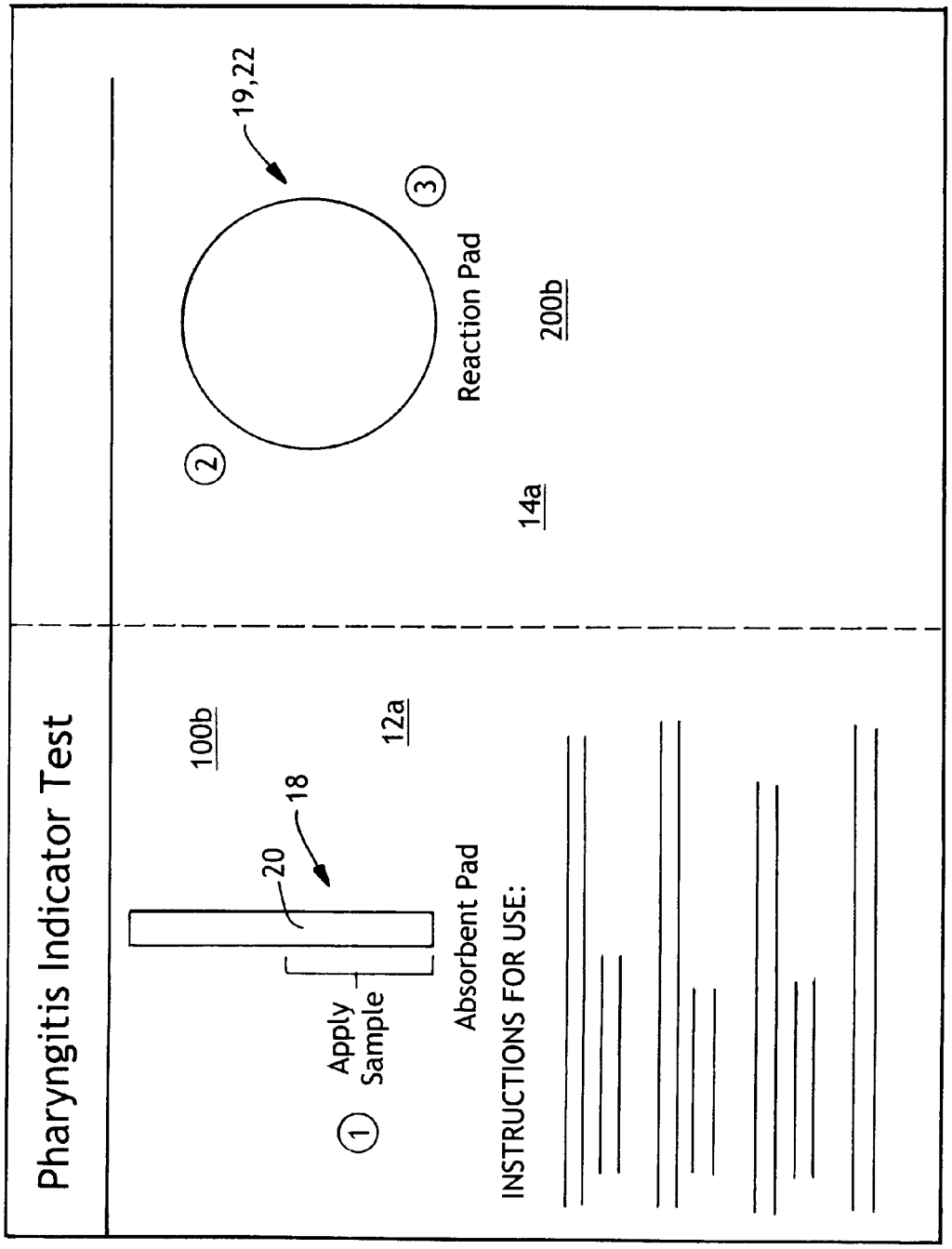
Figure 1C:
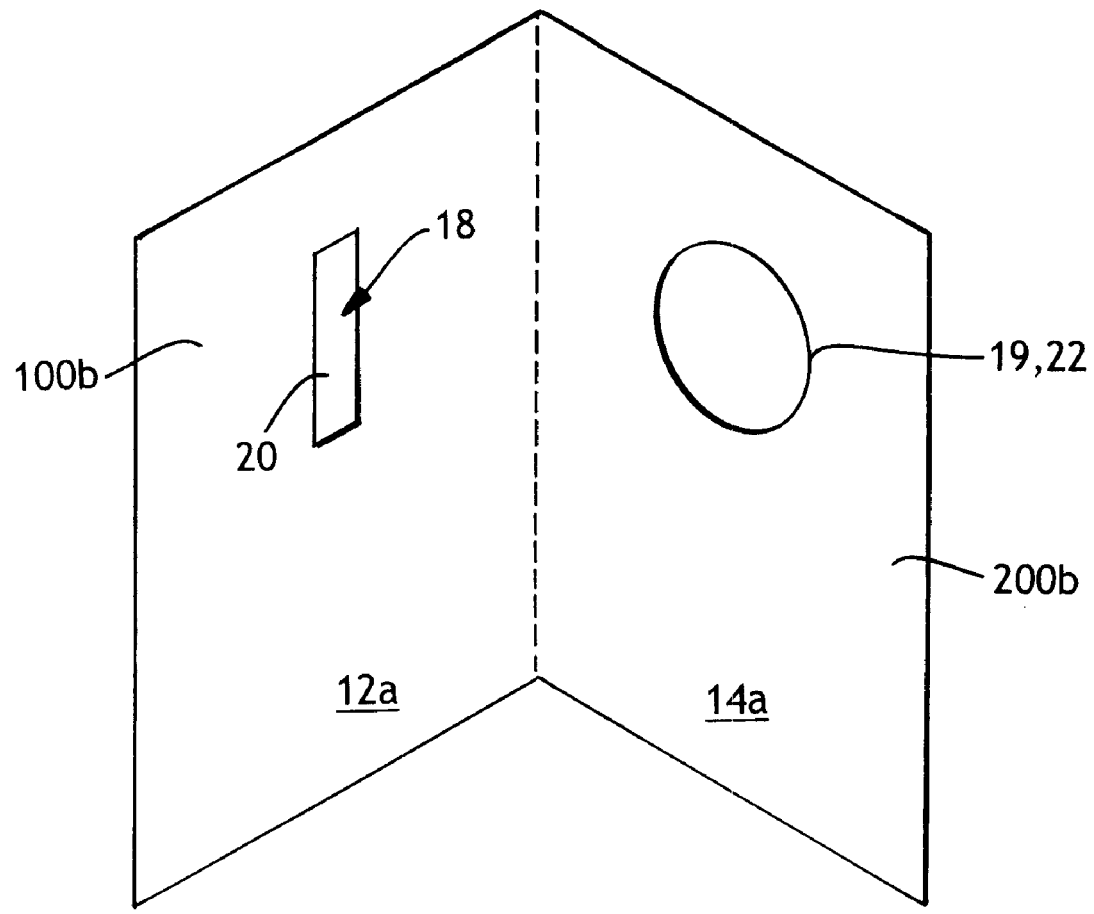
FIG. 1C is a three-dimensional representation of the embodiment shown in FIGS. 1A and 1B showing a card-like, two-leaf test format.
Figure 2A:
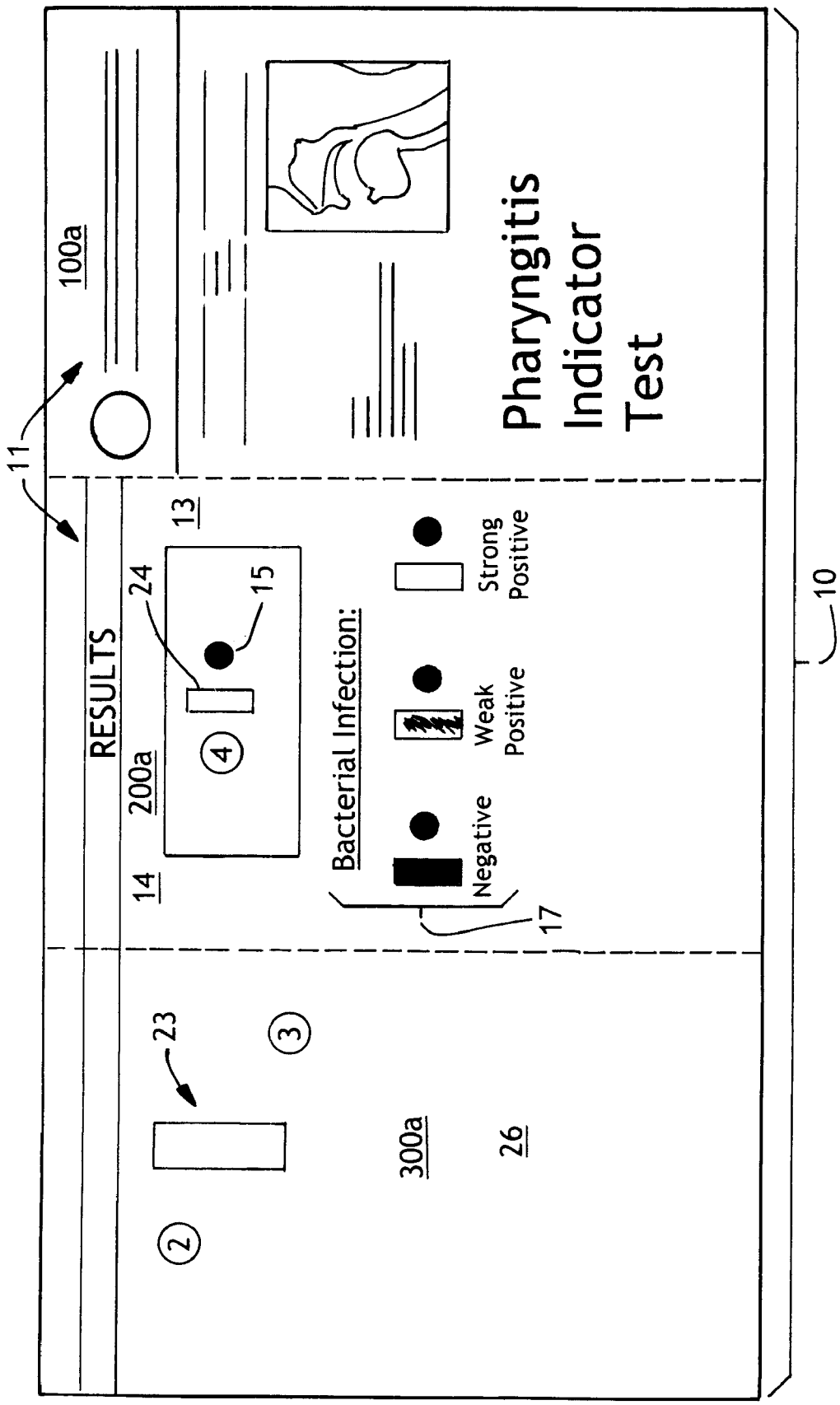
FIGS. 2A and 2B are planar illustrations of a second embodiment of the present invention with a fold-over third panel (300), which is positioned between the first and second panels when in use.
Figure 2B:
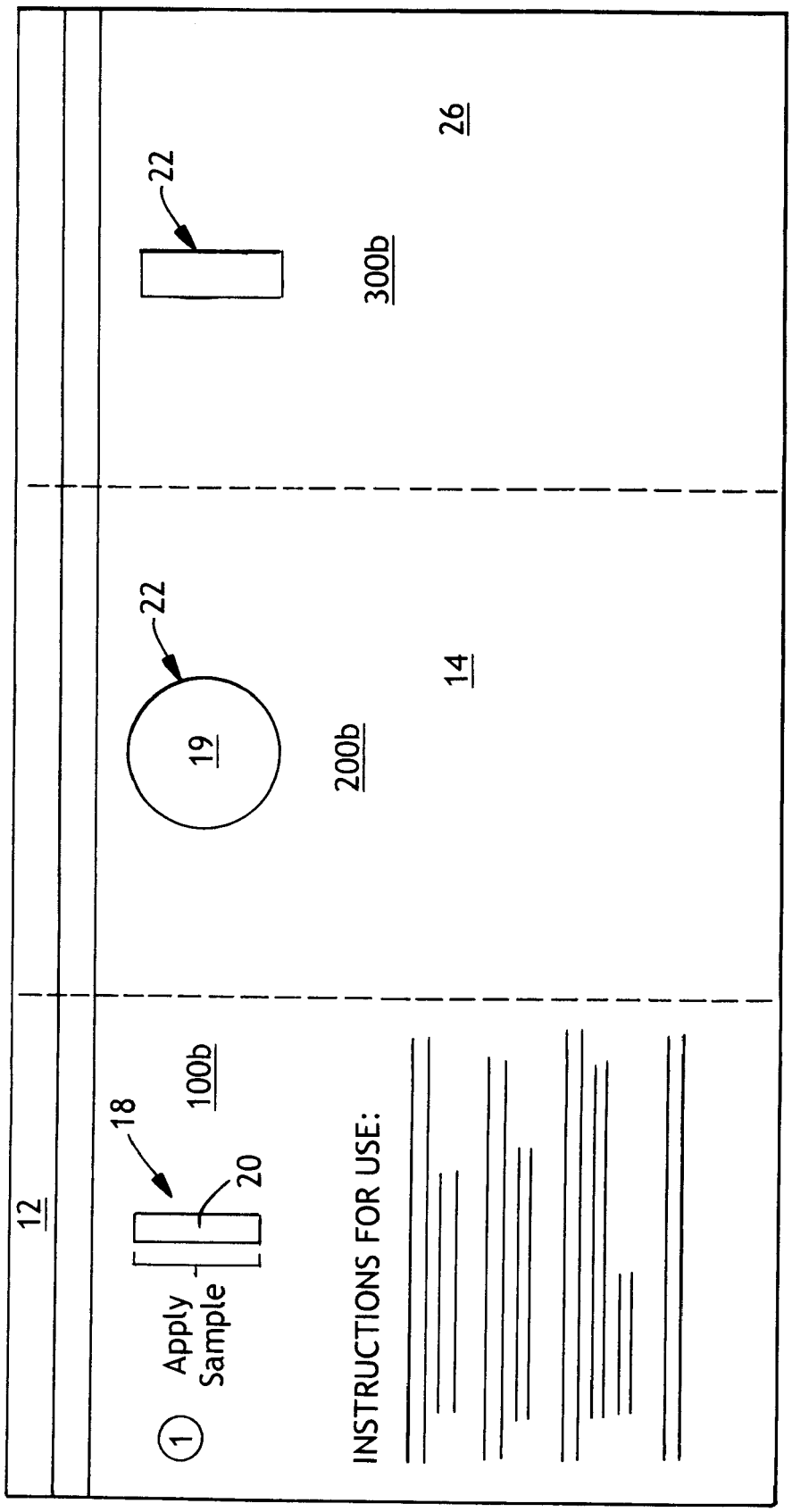
Figure 2C:
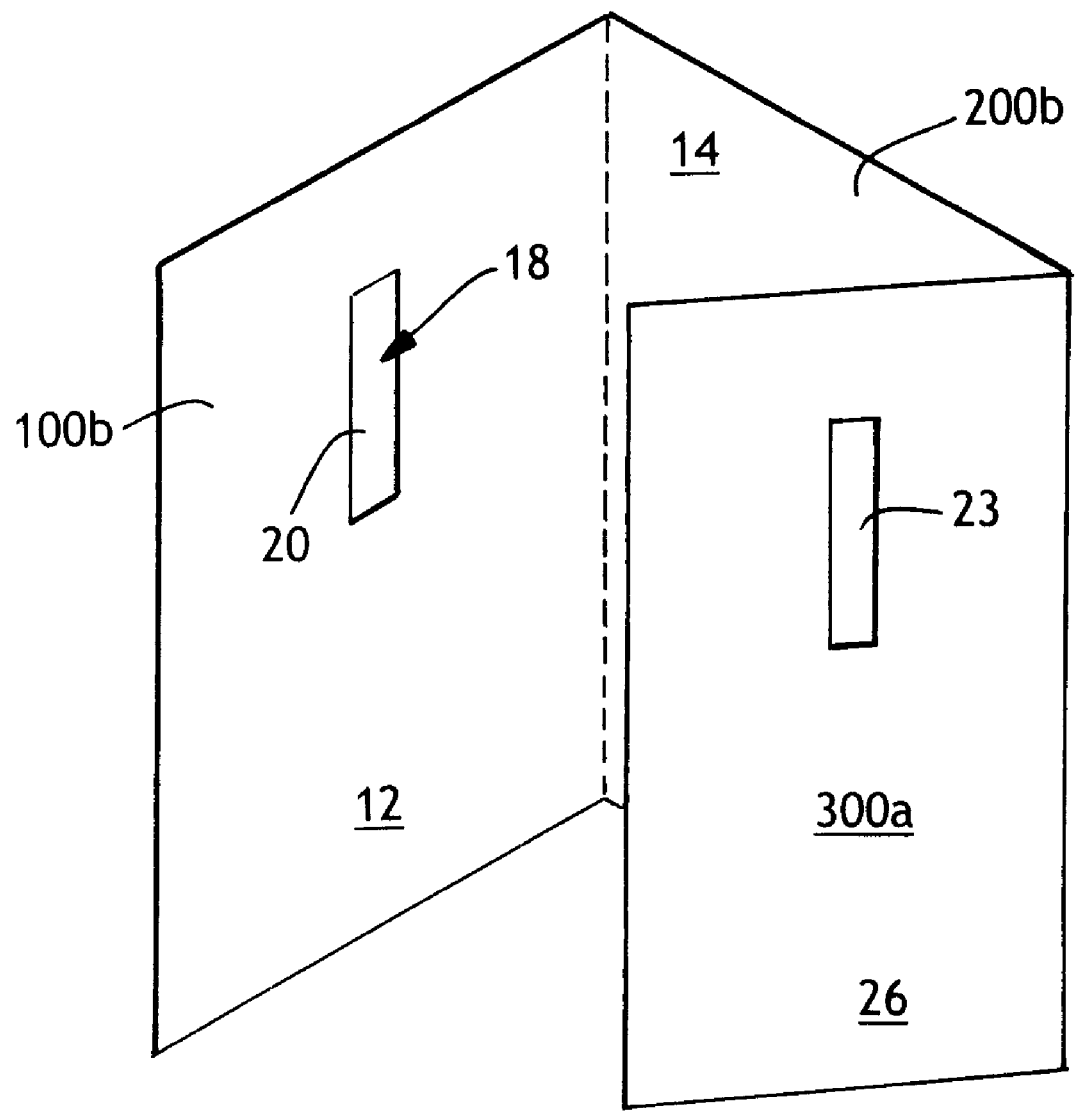
FIG. 2C is a three-dimensional representation of the embodiment shown in FIGS. 2A and 2B, with three panels or leafs.

According to an embodiment, the test indicator device 10 may resemble a folded pamphlet or card-like substrate 11 with at least two opposing leaves or pages. As illustrated in FIGS. 1A, 1B, and 1C the two panels 100, 200 or leaves 12, 14 open away from each other like a bi-fold card or book, according to one embodiment. In another embodiment, such as depicted in FIGS. 2A, 2B, and 2C, one of the two leaves is configured to have a third panel 300, which folds over to create a third flap 16 of a tri-fold structure. Each leaf of the substrate has a first or inner surface 12a, 14a, and a second or outer surface 12b, 14b and the overall structure 10, 11 when closed has a front and back side. A two-leaf pamphlet, such as shown in FIG. 1C, opens to reveal a test-sample-deposition zone 18 or window on an inner surface 12a. The sample deposition zone has an absorbent sample pad 20 to which a sample-containing swab contacts to transfer a biological sample. The absorbent pad (e.g., white) 20 on one side and a colored membrane (e.g., blue) 19, 22 on the opposing side (on the left and right sides, respectively, as depicted in FIG. 1B). Contacting a test sample that contains a positive concentration of pathogens with the dye-impregnated membrane (i.e., reaction pad) 22 will result in a change of color (e.g., from blue to white or yellowish-white). On the back panel 13 of the test substrate or device is situated a test results window 24. Next to the sample results window 24 can be a control 25, as shown in FIG. 1A, or a color reference 15 and data interpretation guide 17 to help the user compare colors when reading the test results, such as illustrated in FIG. 2A. In a commercial embodiment, the entire device may come wrapped to maintain either clean or sterile conditions in a light-protective pouch, which must be opened to retrieve the assay device.

When the panels are properly folded, the results visualizing window 24 is aligned along an axis of sight with the sample contacting zone 18 and detection zone 22, which communicates the test results to a user. The absorbent pad 20 and sample contacting zone 18 can be located on a part of a first panel or substrate and the solvatochromic dye 19 and detection zone 22 situated on an opposing part of the same substrate. As such, the first and opposing substrates can be two leaves 12, 14, or parts of the same substrate folded over against itself. In other embodiments, the absorbent pad and indicator dye may be placed on separate, discrete first and second substrates. In certain configurations, such as the embodiment of FIGS. 2A-C, a third leaf or flap 26 of the same substrate (of either the first or second substrates), and can be situated between the sample contacting zone and detection zone when folded over against itself. When a third leaf is present, the third leaf 15 has a cut-out reaction window 23 that aligns with the sample contacting zone 18 and detection zone 22, fitting over each of the absorbent pad 20 and indicator dye 19 areas, respectively, of the two zones; such that, when the third leaf 26 is folded over the reaction detection zone 22, the open reaction window 23 sits over the detection zone. The solvatochromic dye probably reacts with acidic residues from a bacterial pathogen in a test sample resulting in a change in color of the solvatochromic dye. The solvatochromic dye does not react with a viral pathogen in a test sample resulting in no change in color.

It is envisioned that, according to certain commercial embodiments, the diagnostic device has certain labeling and product identification markings with printing on a front side, and a back side where the sample results viewing window is located, and two interior panels. When the diagnostic tool is opened like a book, instructions for using the assay and the absorbent pad will be on the left-hand interior panel, and the dye-impregnated membrane (reaction pad) and a aperture or membrane (labeled as "reaction window") will be on the right-hand interior panel. The reaction pad membrane can be covered with a protective film or sheet which is to be removed before applying the sample to the absorbent pad. When the protective covering is peeled away, an adhesive is left behind which allows the device to be "shut" like a book and sealed. This causes the absorbent pad to come into intimate contact with the dye-impregnated reaction pad membrane. Once the dye has reacted with the test sample, the study device can be turned over to observe sample results in the viewing window.

Figure 3:
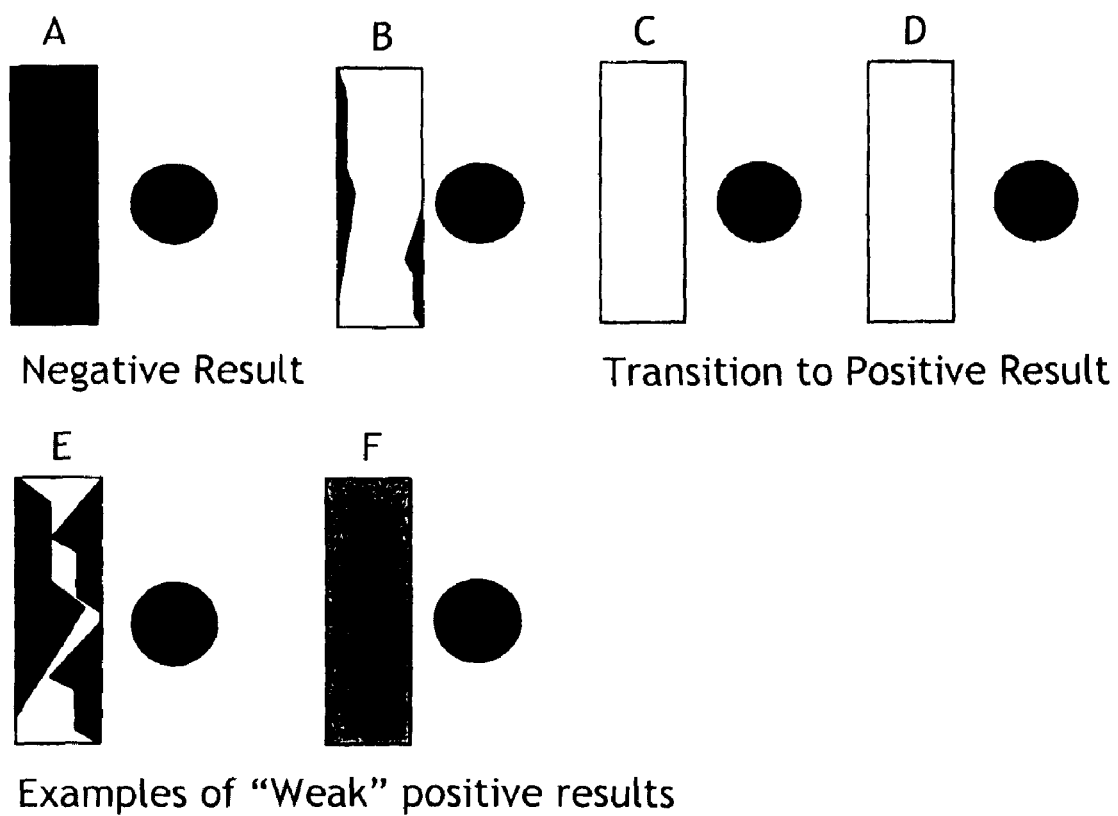
FIG. 3 is a schematic illustration of several possible visual manifestations that communicate whether a bacterial pathogen is present in a test sample, once the sample is applied to a contact zone and reacted with an optically active solvatochromic colorant.

A color reference is given on the back of the test to aid in interpretation of the data. The decolorization of the results window should be judged on how closely the blue color of the reaction pad resembles the blue color of the color reference. If both remain blue, the results are negative. If the blue color of the results window disappears either completely or almost completely by turning white or yellowish-white, this should be interpreted as a positive result. In the blue color disappears only slightly (becomes lighter blue as opposed to white or yellowish-white), this should be interpreted as a weak positive. (See FIG. 3, for some examples of results and their suggested interpretation.)

The substrate has words, numbers, schematic figures, or symbols that communicate instructions to a user to perform an operational sequence for using the detection device. Generally the instructions for use can provide that the user (1) apply a throat swab sample to the absorbent pad, (21) remove the protective cover sheet over the reaction pad, (3) press the absorbent pad to contact reaction pad, and (4) view results through window. A number of schematics or symbols, which provide a comparison of visual manifestations, are located on the second-leaf outer surface proximal to the results window. The schematics or symbols can show relative levels of either negative or positive (e.g., weak or strong) results. In other iterations, the schematics or symbols may manifests as either a "+" or "−" sign, FIG. 1A. The relative color change and/or clarity of the signal development can be employed to reflect the relative level of microbial concentration in the sample, such as depicted in the comparative bacterial infection section of FIGS. 1A (17), 2A (17), and 3E and F. A control color reference for ease of visual comparison can be located near to the results viewing window.

The present device can be made from a variety of materials. The substrates that support the sample contacting and reaction zones can be constructed from semi-rigid materials, for instance, a paper or cardboard stock of either a light or medium weight, KIMDURA™ (a plastic paper), a plastic film (e.g., polyethylene, polypropylene, nylon, polyester, polybutylene, polylactone, or polystyrene), or nitrile or rubber latex. Other materials may include a nonwoven material from polypropylene or polyethylene, for example, spunbond (SB), meltblown (MB), spunbond-meltblown-spunbound (SMS), or spunbond-film laminate (SFL). Organic substrate materials may include cotton or silk fibers, wood, or nitrocellulose. Inorganic substrate materials may include glass or ceramics, and metal foil or sheets. The substrate may include, in part, laminates or combinations of two or more of the kinds of materials mentioned above. The results viewing window can either be open or have a transparent plastic film.

The absorbent pad 20 may be constructed from a porous membrane 28 of a hydrophilic material. The porous membrane, for example, may be formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, glass, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon): porous gels, such as silica gel, agarose, dextran, and gelatin; polymeric films, such as polyacrylamide; and so forth. In a particular embodiment, the porous membrane 28 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The pores of the membrane 23 may have an average size of from about 1 micron to about 50 microns, in some embodiments from about 5 microns to about 30 microns, and in some embodiments from about 5 microns to about 15 microns. The size and shape of the porous membrane 23 may also vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

The support substrate 11 may be positioned directly adjacent to the porous membrane 21 as shown in FIG. 1, or one or more intervening layers may be positioned between the porous membrane 20 and the support substrate 11. If one desires, the support 11 may be formed from a material that is transmissive to light, such as transparent or optically diffuse (e.g., translucent) materials. Also, it is generally desired that the support 11 is liquid-impermeable so that fluid flowing through the membrane 23 does not leak through the support 11. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the porous membrane 21, the support 11 is generally selected to have a certain minimum thickness. Likewise, the thickness of the support 11 is typically not so large as to adversely affect its optical properties. Thus, for example, the support 11 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

As is well known the art, the porous membrane 21 may be set onto the support 11, wherein the resulting laminate may be die-cut to the desired size and shape. Alternatively, the porous membrane 21 may simply be laminated to the support 11 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley, III, et al., which is incorporated herein in its entirety by reference thereto for all purposes.

Section II.—Colorant

A colorant or indicating dye is employed in the present detection device. The colorant or dye can provide a broad spectrum response for bacteria or other microorganisms that is different than its response for viruses. The solvatochromic dye in the colorant indicator zone is believed to be sensitive to certain acidic residues on bacterial cell surfaces, and changes color when a positive test sample makes contacted with the solvatochromic dye. For example, an effective solvatochromic dye-based diagnostic may include Reichardt's dye to differentiate between bacterial and viral pharyngeal infections.

Solvatochromatic indicators are particularly effective in undergoing a distinct color change in the presence of a broad spectrum of bacteria or other microorganisms, yet very little if any change in the presence of viruses associated with upper respiratory conditions. An example of a type of solvatochromatic indicator that may be employed in the present invention is merocyanine indicators (e.g., mono-, di-, and tri-merocyanines). Merocyanine indicators, such as merocyanine 540, fall within the donor-simple acceptor indicator classification of Griffiths as discussed in "Colour and Constitution of Organic Molecules" Academic Press, London (1976). More specifically, merocyanine indicators have a basic nucleus and acidic nucleus separated by a conjugated chain having an even number of methine carbons. Such indicators possess a carbonyl group that acts as an electron acceptor moiety. The electron acceptor is conjugated to an electron donating group, such as a hydroxyl or amino group. The merocyanine indicators may be cyclic or acyclic (e.g., vinylalogous amides of cyclic merocyanine indicators). For example, cyclic merocyanine indicators generally have the following structure:

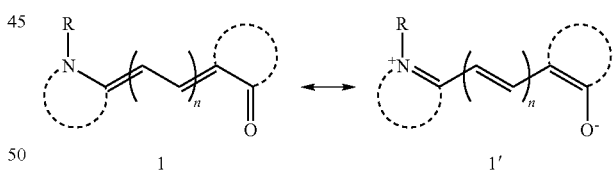

wherein, n is any integer, including 0. As indicated above by the general structures 1 and 1', merocyanine indicators typically have a charge separated (i.e., "zwitterionic") resonance form. Zwitterionic indicators are those that contain both positive and negative charges and are net neutral. but highly charged. Without intending to be limited by theory, it is believed that the zwitterionic form contributes significantly to the ground state of the indicator. The color produced by such indicators thus depends on the molecular polarity difference between the ground and excited state of the indicator. One particular example of a merocyanine indicator that has a ground state more polar than the excited state is set forth below as structure 2.

9

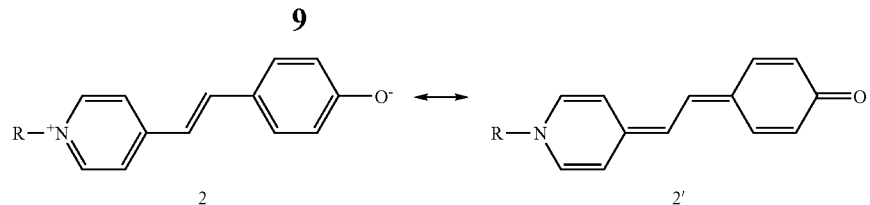

The charge-separated left hand canonical 2 is a major contributor to the ground state whereas the right hand canonical 2' is a major contributor to the first excited state. Still other examples of suitable merocyanine indicators are set forth below in the following structures 3-13.

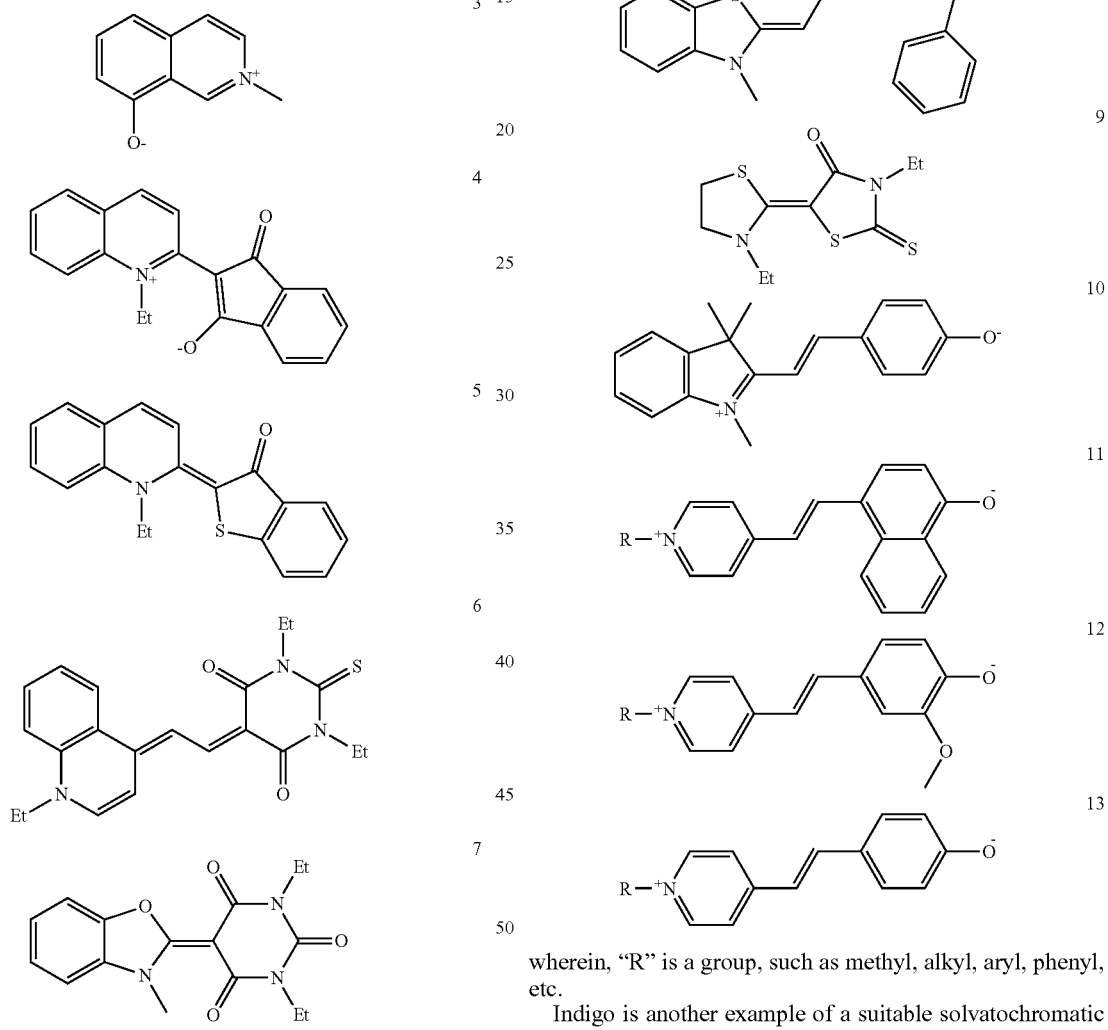

wherein, "R" is a group, such as methyl, alkyl, aryl, phenyl, etc.

Indigo is another example of a suitable solvatochromatic indicator for use in the study article. Indigo has a ground state that is significantly less polar than the excited state. For example, indigo generally has the following structure 14:

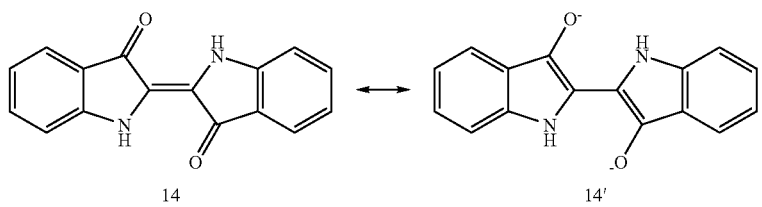

The left hand canonical form 14 is a major contributor to the ground state of the indicator, whereas the right hand canonical 14' is a major contributor to the excited state.

Other suitable solvatochromatic indicators that may be used in the detection device include those that possess a permanent zwitterionic form. That is, these indicators have formal positive and negative charges contained within a contiguous π-electron system. Contrary to the merocyanine indicators referenced above, a neutral resonance structure cannot be drawn for such permanent zwitterionic indicators. Exemplary indicators of this class include N-phenolate betaine indicators, such as those having the following general structure:

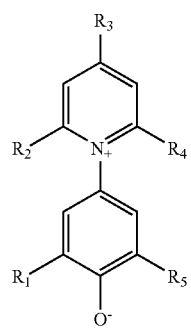

wherein $R_1$-$R_5$ are independently selected from the group consisting of hydrogen, a nitro group (e.g., nitrogen), a halogen, or a linear, branched, or cyclic $C_1$ to $C_{20}$ group (e.g., alkyl, phenyl, aryl, pyridinyl, etc.), which may be saturated or unsaturated and unsubstituted or optionally substituted at the same or at different carbon atoms with one, two or more halogen, nitro, cyano, hydroxy, alkoxy, amino, phenyl, aryl, pyridinyl, or alkylamino groups. For example, the N-phenylolate betaine indicator may be 4-(2,4,6-triphenylpyridinium-1-yl)-2,6-diphenylphenolate (Reichardt's dye) having the following general structure 15:

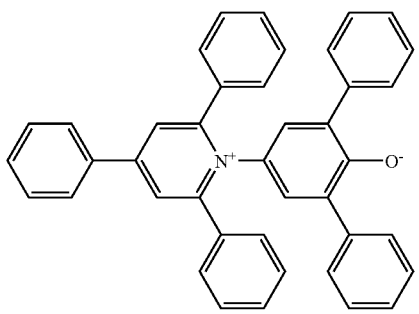

Reichardt's dye shows strong negative solvatochromism and may thus undergo a significant color change from blue to colorless in the presence of bacteria. That is, Reichardt's dye displays a shift in absorbance to a shorter wavelength and thus has visible color changes as solvent eluent strength (polarity) increases. Still other examples of suitable negatively solvatochromatic pyridinium N-phenolate betaine indicators are set forth below in structures 16-23:

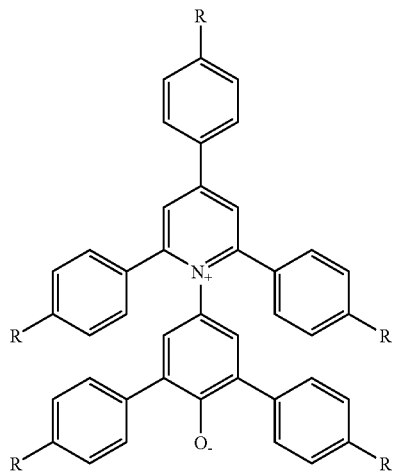

wherein, R is hydrogen, —$C(CH_3)_3$, —$CF_3$, or $C_6F_{13}$.

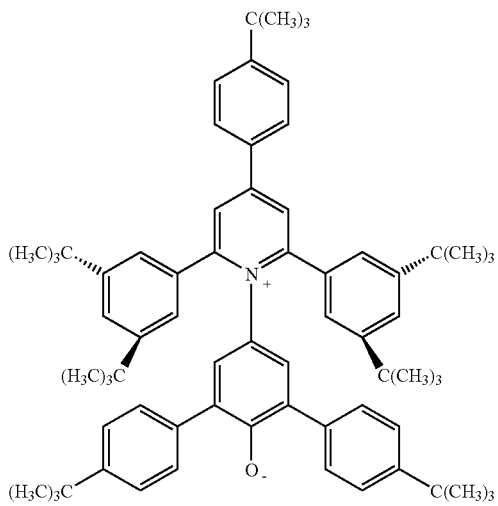

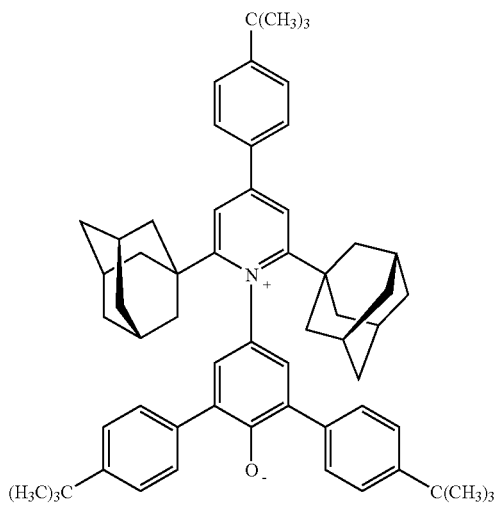

Still additional examples of indicators having a permanent zwitterionic form include indicators having the following general structure 24:

$$\text{structure 24}$$

wherein, n is 0 or greater, and X is oxygen, carbon, nitrogen, sulfur, etc. Particular examples of the permanent zwitterionic indicator shown in structure 24 include the following structures 25-33.

Still other suitable solvatochromatic indicators may include, but are not limited to 4-dicyanmethylene-2-methyl-6-(p-dimethylaminostyryl)-4H-pyran (DCM); 6-propionyl-2-(dimethylamino)naphthalene (PRODAN); 9-(diethylamino)-5H-benzo[a]phenox-azin-5-one (Nile Red); 4-(dicyanovinyl) julolidine (DCVJ); phenol blue; stilbazolium indicators; coumarin indicators: ketocyanine indicators; N,N-dimethyl-4-nitroaniline (NDMNA) and N-methyl-2-nitroaniline (NM2NA); Nile blue; 1-anilinonaphthalene-8-sulfonic acid (1,8-ANS), and dapoxylbutylsulfonamide (DBS) and other dapoxyl analogs. Besides the above-mentioned indicators, still other suitable indicators that may be used in the present invention include, but are not limited to, 4-[2-N-substituted-1,4-hydropyridin-4-ylidine)ethylidene]cyclohexa-2,5-dien-1-one. red pyrazolone indicators, azomethine indicators, indoaniline indicators, and mixtures thereof.

The reaction pad base material is an ANODISC™ Membrane Filter (Whatman® Inc, Florham Park, N.J.). The absorbent pad material is the Hi-Flow™ Plus HF120 Membrane provided by Millipore (Billerica, Mass.). Reichardt's dye is manufactured by Tyger Scientific, Inc (Ewing, N.J.).

In other iterations of the present invention, we envision including a control, such as a fatty or dry acid striped onto an absorbent membrane or an actual bacteria control striped onto the membrane upstream of the reaction zone. The sample could wick up a strip and the accompanying fluid would release the acid or microbe to react with the solvatochromic colorant (e.g., Reichardt's dye).

An advantage of the present diagnostic tool is the relatively fast reaction time and diagnostic clarity of the color change signal. The color change generally occurs within about 30 minutes of the test sample contacting with the solvatochromic dye in the colorant reaction zone. Typically, the reaction occurs in under about 20-25 minutes, ideally in less than 10-15 minutes, and most desirably within about 5-10 minutes. In certain embodiments the reaction time can be as quickly as 1-3 minutes. The reaction time can be correlated to the relative severity or extent of bacterial infection. A color change can vary in development time depending on the concentration (in CFU/mL) of bacteria in a test sample.

Detection of the final result could occur visually by means of the naked eye, or with the assistance of an electronic or digital reader, scanner, web cam, or other optical imaging system, such as presently available. Apart from the naked eye, the relative intensity and color range of the solvatochromic dye can be better or more accurately monitored using an optical reader. Furthermore, results could be interpreted through either a color change on a membrane. or through a secondary indicator, such as an LCD light which is turned on due a change in electrochemistry of the dye brought on by contact with a microbe. Results could be interpreted by means of the comparative difference in the rate of change in de-colorization of the dye. The interpretation of results could also occur by the creation of a "+" sign with a positive test compared to a "−" sign, as a default setting.

B

Section III.—Empirical Examples

Laboratory testing has shown that solvatochromic dyes, such as Reichardt's dye, are a promising method to detect a wide variety of bacteria, as well as distinguish bacterial infections from viral infections. When using Reichardt's dye as the indicator colorant, it discolors from a solid dark teal/blue to colorless in the presence of bacteria, but not viruses (or to a much lesser extent that is distinctly observable).

The particular design of the present diagnostic device does not require either the patient or the physician to contact the indicator dye. Rather, it is desirable that a test sample is deposited or contacts the absorbent pad via a swab conduit. For instance, a sterile swab can be applied to a patient's pharynx and tonsils (if present) to obtain a sample in the same manner as specimen collection for a culture. The sample-containing swab is then contacted with the test sample zone, thus avoiding any direct contact of the reaction pad with the patient or healthcare practitioner Alternatively, the sample could be applied to the device via a swab or some direct sampling method, such as saliva, blood, tears, etc. The swab itself could also be used to house the device such that the color change would occur on a portion of the swab when the fluid is wicked through the tip. The swab or sampling mechanism could also contain any number of well-known microfluidic components to channel and concentrate any sample. A diluent pack could also be employed to add fluid for wicking purposes.

The following examples demonstrate the efficacy of the present detection mechanism for differentiating between bacterial versus viral pathogens.

1. Initial Testing of Indicator Dye with *S. aureus, P. aeruginosa*, and *E. coli*

A solution of Reichardt's dye (0.5 g of dye in 20 g of acetonitrile) was prepared and placed onto a proprietary absorbent substrate and allowed to air dry. The Reichardt's dye-coated sheets were tested for color change visible to the eye using the following microorganisms listed in USP (United States Pharmacopoeia) XXIV as opportunistic pathogens: *S. aureus* (ATCC #6538), *E. coli* (ATCC #8739) and *P. aeruginosa* (ATCC #9027). Lyophilized cultures of the above listed organisms were started in 5 ml tubes of sterile trypticase soy broth (TSB) commercially available from Becton Dickinson (BBL) Labs. To maintain stock cultures at the same bacterial cell concentration day to day, one (1) drop (approx. 0.1 ml) was aseptically transferred from each stock culture to a new 5 ml tube of sterile TSB using a sterile transfer pipette. Five (5) culture transfers were made for each organism before any were used for sensitivity testing.

Starting with stock culture concentrations of $10^9$ to $10^8$ CFU (colony forming units)/ml, 1:10 serial dilutions were made using 9 ml volumes of sterile de-ionized water. Depending on the concentration desired, the following dilutions were typically made: $10^7$, $10^6$, $10^5$, $10^4$, and $10^3$ CFU/ml. Viable plate counts were performed on all stock cultures before sensitivity testing started. These counts along with the serial dilutions made, were used to calculate the actual bacterial concentrations for the testing performed.

Reichardt's dye coated proprietary absorbent substrates were tested by taking a 100 μl aliquot of liquid containing the highest concentration of bacteria. The dye turned colorless in the area wet by the bacteria, indicating the presence of bacteria. A similar sized spot of the media liquid that did not contain bacteria did not change color. The experiment continued with the less-concentrated bacteria aliquots until the spot did not show a visible change. The lower limit for indication of gram-negative bacteria was found to be 1000 CFU/ml and for gram-positive bacteria as low as 100 CFU/ml.

2. Testing with *Salmonella* Bacteria

In a similar fashion, the Reichardt's dye coated proprietary absorbent substrates were tested with a *Salmonella*-containing liquid. Gibraltar Labs (Fairfield, N.J.) placed 100 microliter aliquots of the solutions onto the absorbent substrate. The wet spots turned white indicating that the *Salmonella* decolorized the dye. Hence the dye is sensitive to *Salmonella*. The media alone or water was also placed onto the towel and did not appreciably decolorize the coating.

3. Testing with Additional Microorganisms

We discovered during testing that a solution of Reichardt's dye could be used to semi-quantitatively assess microbial concentration. To do so, a drop of a desired microbe could be placed on an absorbent substrate. Reichardt's dye solution could then be added drop wise to this spot until the blue color persisted rather than being rapidly de-colorized. $10^7$ CFU/ml of *S. aureus. C. albicans, G. vaginalis, E. coli, P. aeruginosa*, and *L. acidophilus* were pipetted onto a proprietary absorbent substrate (100 μl each). In addition, $10^5$ CFU/mL of *A. niger* was also pipette onto the absorbent substrate. Reichardt's dye (160 mg in 10 g of acetonitrile) was then added in 10 μl aliquots to each spot and the numbers of drops needed to establish a persistent color were counted.

The amount of dye required to maintain a persistent purple color for each organism is provided in Table 1. The strongest reaction was observed with *L. acidophilus*, followed by *S. aureus, G. vaginalis, E. coli, P. aeruginosa, C. albicans*, and finally *A. niger*. Results suggested that organisms vary in their ability to de-colorize the dye, with some provoking a faster/more intense reaction than others.

TABLE 1

Titration of Various Microorganisms with Reichardt's Dye

| Compound | Type | Amount of Dye Required for Persistent Color (μl) |
| --- | --- | --- |
| Lactobacillus | gram(+) | 110 |
| S. aureus | gram(+) | 90 |
| G. vaginalis | gram(−) | 90 |
| E. coli | gram(−) | 90 |
| P. aeruginosa | gram(−) | 80 |
| C. albicans | yeast | 70 |
| A. niger | mold | 50 |

Testing was also conducted with bacterial spores such as *Anthracis bacillus*. The data from those tests suggest that Reichardt's dye (as tested) was not sufficiently sensitive to bacterial spores. Testing with the vegetative organism, however, showed that de-colorization occurred, indicating that the dye was insensitive to the spore coat, not the actual organism. Thus, when trying to detect bacterial spores, it may first be necessary to chemically pre-treat a sample such that the spore coat is removed.

4. Rapid Quantification of Bacteria Using an Indicator-treated Surface

Neenah brand paper was coated with Reichardt's dye solution (80 mg/10 g acetonitrile) and hung to dry. Aliquots (100 μL) of *S. aureus*, were used to create a standard curve. A hand-held spectrophotometer was used to generate a numerical standard curve by plotting Delta E (calculated using $L^*$, $A^*$, and $B^*$ values obtained by spectrophotometer using the CIELAB method) against log CFU/mL concentrations.

Figure 4:
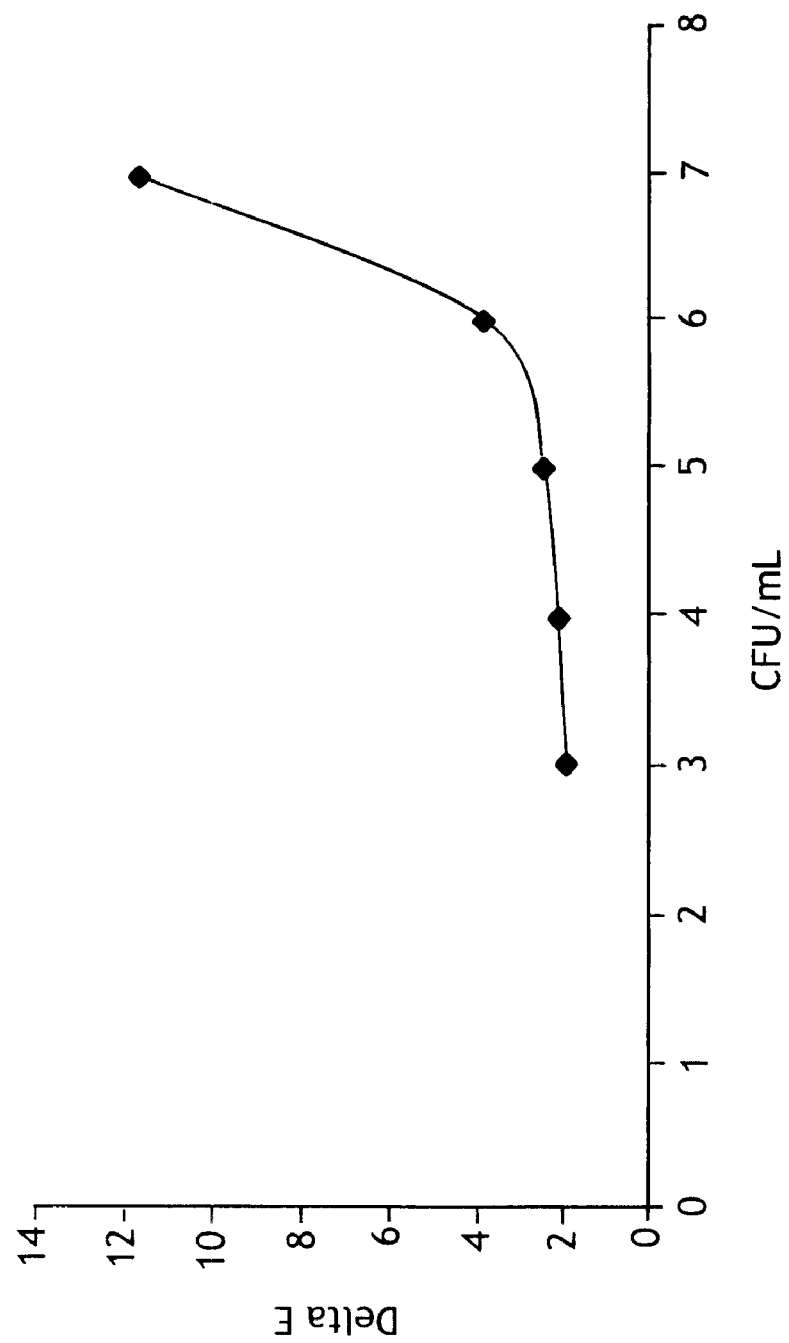
FIG. 4 is a standard curve for S. aureus, comparing optical measurements ($\Delta E$ values) of color change against a unit concentration of bacteria present.

Optical measurements (Delta E values) generated from the standard curve were used to create the plot shown in FIG. 4. "1" (on the y-axis) represents a "just perceptible" color-change. Results confirm that the color changes previously observed by eye are, in fact, detectable and distinguishable from one another using a spectrophotometer. Furthermore, the results indicate that the responsiveness of the dye to the *S. aureus* bacteria is dose-dependent, and appears to taper off as the concentration of bacteria decreases.

5. Testing with Additional Solvents The de-colorization reaction observed with Reichardt's dye has been investigated thoroughly and found to occur when the dye is dissolved in a variety of solvents such as isopropanol, acetonitrile, ethanol, dimethylformamide, octanol, and methanol. It has also been discovered that the dye can be dissolved in a variety of detergents such as Tween) and still retain its reactivity, particular when a carrier solvent such as isopropanol is utilized as well.

6. Testing with Bacterial Cell-Wall Components

Insight into how this indicator technology works was obtained by utilizing molecules commonly found in the cell walls of bacteria. Although there is some commonality in the compounds which comprise the surfaces of gram-positive and gram-negative bacteria, their arrangement and chemical composition differ from one another. Gram-negative bacteria have an outer membrane coated with lipopolysaccharide (LPS). LPS lends a net-negative charge to the surface of gram-negative bacteria and contributes to its pathogenesis. Gram-positive bacteria are coated with a thick peptidoglycan, or murein, sheet-like layer. The sheets are formed from alternating N-acetylglucosamine and N-acetylmuramic acid molecules. Teichoic acids are also found in gram-positive bacteria and may be linked to the N-acetylmuramic acid. While gram-negative bacteria also have peptidoglycan, the layer on gram-positive bacteria is much thicker.

Solutions of *E. coli*-derived detoxified lipopolysaccharide (LipidA component removed), lipoteichoic acid derived from *Streptococcus faecalis, E. coli*-derived lipopolysaccharide, and muramic acid (Sigma-Aldrich, St. Louis, Mo.) were placed onto a dye-coated proprietary absorbent substrate. With the exception of the pure LPS, all solutions were prepared in 5% (wt/wt), 1% (wt/wt), and 0.2% (wt/wt) concentrations. Pure LPS was prepared in 0.1% (wt/wt), 0.02% (wt/wt), and 0.004% (wt/wt) for safety reasons.

As an additional experiment, solutions of *E. coli*-derived detoxified lipopolysaccharide Lipid A component removed), lipoteichoic acid derived from *Streptococcus faecalis, E. coli*-derived lipopolysaccharide, and muramic acid were placed onto a proprietary absorbent substrate. With the exception of the pure LPS, all solutions were prepared in 5% (wt/wt), 1% (wt/wt). and 0.2% (wt/wt) concentrations. Pure LPS was prepared in 0.1% (wt/wt), 0.02% (wt/wt). and 0.004% (wt/wt) for safety reasons. Reichardt's Dye (160 mg in 10 g acetonitrile) was added in 10 μl aliquots to each spot and amount of dye required to produce a persistent color was recorded.

Figure 5:
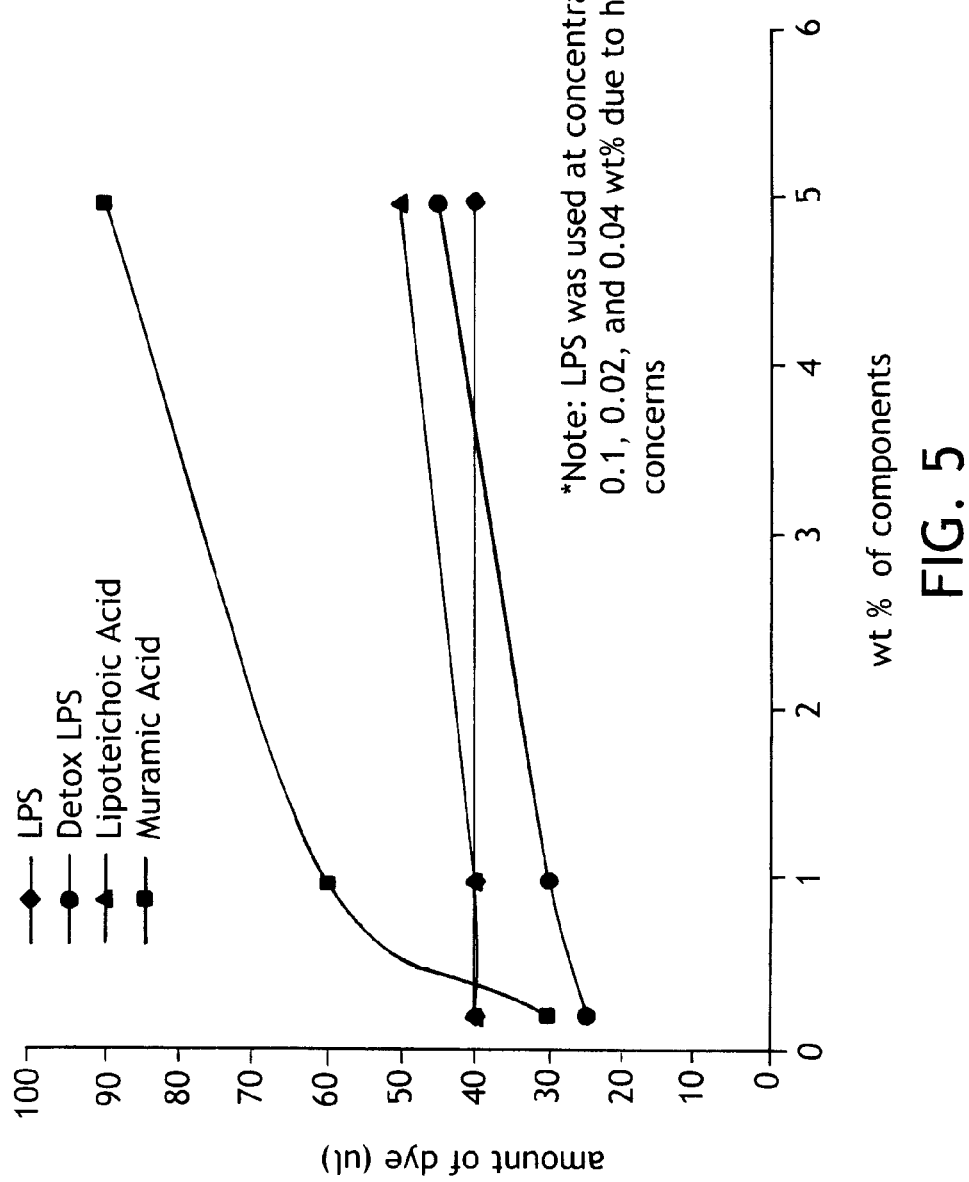
FIG. 5 is a titration curve of bacterial cell-wall components against indicator dye concentration.
Figure 6:
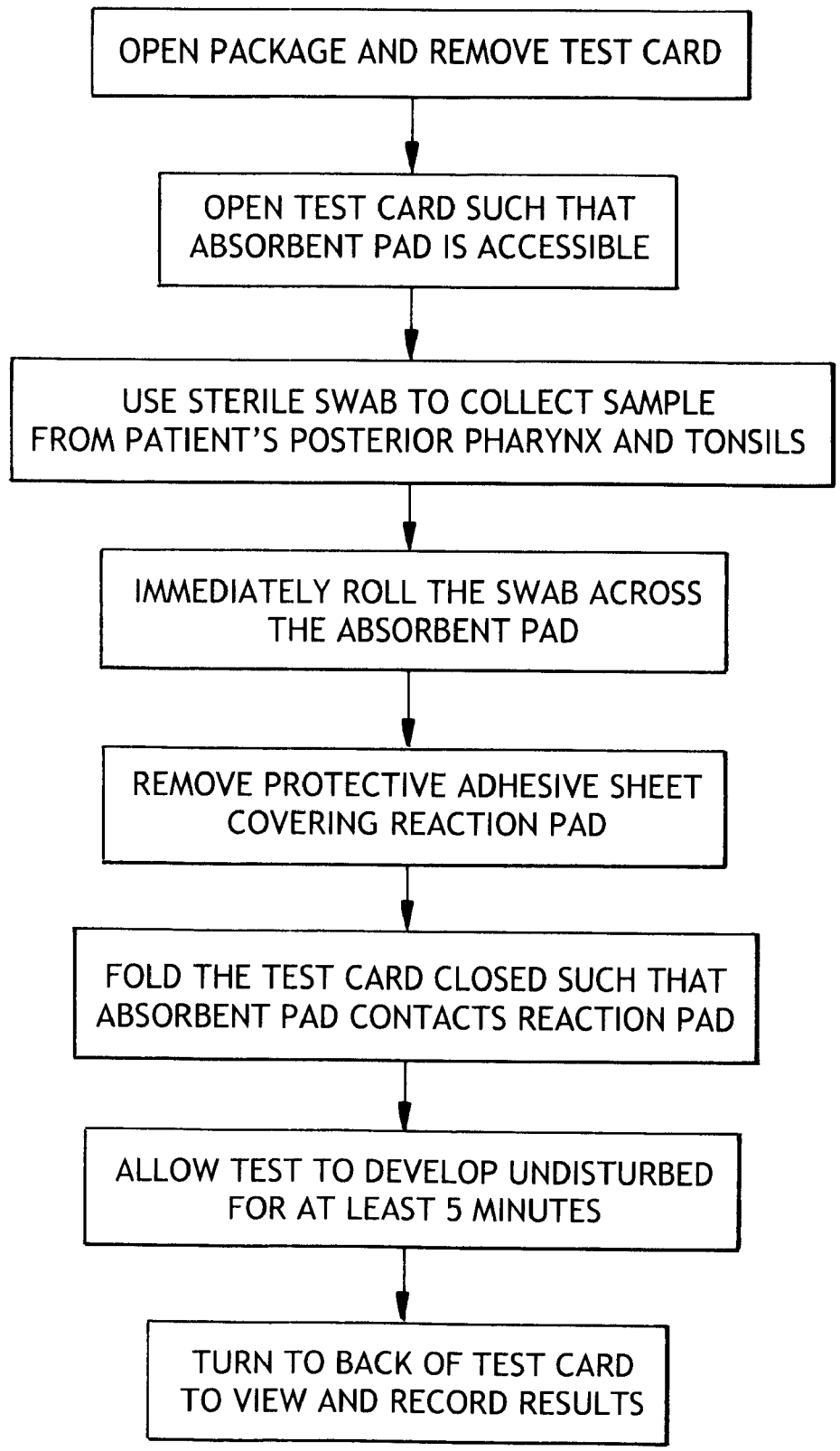
FIG. 6 is an example of a schematic flow-chart that demonstrates a protocol or method of using an iteration of the present invention.

Muramic acid produced the strongest reaction, resulting in a near instantaneous de-colorization of the dye in both experimental set-ups. The other compounds did cause eventual de-colorization of the dye, but did not appear to react as strongly as muramic acid. Because muramic acid is found in greater concentrations on gram-positive bacteria, these results demonstrate the potential of this dye to not only give CFU/mL data, but also to distinguish between gram-positive and gram-negative bacteria based on strength and speed of reaction. Results from the titration experiment are provided in FIG. 5.

7. Testing with Autoclaved Bacteria

In order to verify that the bacterial cell wall plays a critical role in this reaction, a vial of S. aureus ($10^6$ CFU/mL) was autoclaved before testing with the indicator spray (160 mg Reichardt's Dye in 10 g of isopropanol). Autoclaving kills bacteria by essentially blowing the cell wall apart. The steam from the autoclave penetrates the bacteria and rips the membrane apart. When the solution autoclaved S. aureus was pipette onto a surface and sprayed with the Reichardt's dye indicator spray (160 mg in 10 g isopropanol), no de-colorization was observed. This data suggests that an intact cell wall may be required for de-colorization of the Reichardt's dye by bacteria.

8. Testing with Protoplasts

An additional test to verify reaction with the cell wall was performed by creating protoplasts through enzymatic digestion of the bacterial cell wall. Briefly, 1 mL of S. aureus ($10^8$ CFU/mL) was reacted with 9 mL of 200 μg/mL egg white lysozyme (Sigma-Aldrich, St. Louis, Mo.) suspended in TM buffer (0.05 M Tris-HCl, pH 7.4, 20 mM $MgCl_2$) with 15% (w/v) of sucrose (Sigma-Aldrich, St. Louis, Mo.). The reaction was carried out for one hour at 30° C., after which the solution was centrifuged at 10,000×g, and rinsed twice with TM buffer containing 13% (w/v) sucrose according to methods detailed by Taku and Fan (*The Journal of Biological Chemistry*, 1979).

The solution containing protoplasts was reacted (100 μL aliquot) with an Avery label coated with Reichardt's dye (80 mg/10 g acetonitrile). Untreated bacteria was diluted 10 fold in the TM/13% sucrose buffer (without lysozyme) and were placed on the label as a positive control. After approximately 5 minutes, the bacterial solutions were sucked off the surface, revealing de-colorization from the untreated positive control, but minimal de-colorization from the solution thought to contain protoplasts.

To confirm that protoplasts were indeed created, a gram stain was performed on the sample. Gram-staining showed uptake of the crystal violet stain by a S. aureus control, while the protoplast-containing sample did not exhibit dye uptake. This suggests that the cell wall was effectively removed as gram positive organisms such as S. aureus should show staining of the cell wall as part of the gram stain procedure.

To confirm that the suspected protoplasts were actually viable organisms and were not irrevocably damaged during the experimental process, aliquots of the protoplast solution as well as the positive control (in TM/13% sucrose) were plated and cell counts taken the following day. Counts for the protoplast and control solutions were $7.9 \times 10^8$ CFU/ml and $5.9 \times 10^8$ CFU/ml, respectively, indicating that the protoplasts were viable and that cell numbers were not diminished during the experimental procedure.

In summary, experimental findings from reaction with protoplasts suggest that the presence of the cell wall is critically important for de-colorization of Reichardt's dye by bacteria. Thus, processes or conditions which damage the cell wall may reduce sensitivity of the Reichardt's dye to bacteria.

9. Testing with Upper Respiratory-Related Pathogens

In some examples using Reichardt's dye-treated samples, the samples were reacted with 100 microliters of each of the following bacteria: *Haemophilus influenzae* (ATCC # 49247) (*H. influenzae*), *Moraxella lacunata* (ATCC # 17972) (*M. lacunata*), *Streptococcus pyogenes* (ATCC # 10782) (*S. pyogenes*), *Streptococcus pneumoniae* (ATCC # 10015) (*S. pneumoniae*). The following virus species were also tested: Rhinovirus Type 42 (Received May 13, 1982 from Hoffman La Roche), Influenza A (ATCC # VR-544), Adenovirus Type 2 (ATCC # VR-846), Adenovirus Type 5 (ATCC # VR-5).

Studies showed that the dye-treated samples were de-colorized by these pathogenic organisms, particularly *S. pyogenes* and *S. pneumonia*. It has been observed in prior experiments that gram positive bacteria elicit a stronger de-colorization response than other types of microorganisms.

Testing with Rhinovirus, Influenza, and Adenovirus showed markedly less de-colorization of the dye that what was observed from a *Salmonella* bacterial control at a similar concentration. Comparison to the media control also showed the de-colorization observed to be minimal. Adenovirus, in particular, showed almost no ability to de-colorize the dye.

In another example, several of the present assay devices are tested with *S. pyogenes, S. pneumonia*, MRSA, Rhinovirus, and Adenovirus 2. All bacteria were prepared in trypticase soybean broth (TSB) to a concentration of $10^7$ CFU/ml while viruses were prepared in Dulbecco's Modified Eagle Medium (DMEM) with 5% fetal bovine serum (FBS) to a TCID 50 value of roughly $10^{-6.5}$. Additional solutions are made for each microorganism with 5% mucin (and 5% fetal bovine serum (FBS) for bacterial samples). A swab is dipped into each solution and applied to an absorbent pad of a device. The assay is shut and sealed with a topical adhesive. After 5 minutes, we observed that bacterial samples caused a de-colorization of the membrane that was easily seen by the naked eye, while viral samples did not.

The present invention has been described in general and in detail by way of examples. It is believed that the technology embodied in the present indicator test device can provide an efficient, cost effective, and fast acting diagnostic tool, either at home or in the clinical setting, while posing negligible complications or risk to the patient or clinician. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

We claim:

1. A diagnostic aid that distinguishes between bacterial and viral pathogens, said diagnostic aid comprising: an absorbent pad in a sample contacting zone wherein said absorbent pad and sample contacting zone are part of at least a first substrate, an opposing detection zone having a solvatochromic dye, wherein said detection zone and solvatochromic dye are situated on an opposing substrate, and a results visualizing window aligned along an optical axis with said sample contacting zone and detection zone, such that a test sample applied to said absorbent pad contacts said opposing detection zone, reacts with said solvatochromic dye zone, and manifests a visual signal through said results visualizing window.

2. The diagnostic aid according to claim 1, wherein said first and opposing substrates are two leaves or parts of the same first substrate folded over against itself.

3. The diagnostic aid according to claim 1, further comprising a third leaf of the same substrate, and is situated between said sample contacting zone and detection zone when folded over against itself.

4. The diagnostic aid according to claim 3, wherein said third leaf has a cut-out reaction window, which fits over and aligns with said sample contacting zone and detection zone.

5. The diagnostic aid according to claim 2, wherein said solvtochromic dye reacts with a bacterial pathogen in said test sample resulting in a change in color of the solvatochromic dye.

6. The diagnostic aid according to claim 2, wherein said solvatochromic dye does not react with a viral pathogen in said test sample resulting in no change in color of the solvatochromic dye.

* * * * *